United States Patent
Baynham

(10) Patent No.: US 12,383,403 B1
(45) Date of Patent: Aug. 12, 2025

(54) METHOD OF TREATING A MEDICAL IMPLANT SURFACE FOR OSSEOINTEGRATION

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

(*) Notice: Subject to any disclaimer, the term of this patent is extended or adjusted under 35 U.S.C. 154(b) by 799 days.

(21) Appl. No.: 17/657,447

(22) Filed: Mar. 31, 2022

Related U.S. Application Data

(60) Provisional application No. 63/169,652, filed on Apr. 1, 2021.

(51) Int. Cl.
*A61F 2/30* (2006.01)
*B23H 5/04* (2006.01)

(52) U.S. Cl.
CPC .......... *A61F 2/3094* (2013.01); *B23H 5/04* (2013.01); *A61F 2002/30784* (2013.01); *A61F 2002/30838* (2013.01); *A61F 2002/3084* (2013.01); *A61F 2002/3093* (2013.01); *A61F 2002/30978* (2013.01)

(58) Field of Classification Search
None
See application file for complete search history.

(56) References Cited

U.S. PATENT DOCUMENTS

| | | | | |
|---|---|---|---|---|
| 3,851,135 A | * | 11/1974 | Moracz | B23H 1/00 219/69.15 |
| 4,584,450 A | * | 4/1986 | Inoue | B23H 1/08 210/685 |
| 5,349,149 A | * | 9/1994 | Shiraki | C10M 145/28 252/570 |
| 2010/0133238 A1 | * | 6/2010 | Tsai | B23H 1/08 219/69.17 |
| 2011/0245930 A1 | * | 10/2011 | Alley | A61L 27/56 427/2.24 |
| 2016/0143709 A1 | * | 5/2016 | Jang | A61C 8/0013 433/201.1 |
| 2018/0133928 A1 | * | 5/2018 | Jang | B23H 7/38 |
| 2019/0060515 A1 | * | 2/2019 | Richart | A61L 27/50 |

FOREIGN PATENT DOCUMENTS

| | | | | |
|---|---|---|---|---|
| DE | 4012731 A1 | * | 10/1990 | |
| JP | 04054966 A | * | 2/1992 | |
| KR | 20130092855 A | * | 8/2013 | |
| WO | WO-9616611 A1 | * | 6/1996 | A61C 8/00 |
| WO | WO-2004008983 A1 | * | 1/2004 | A61C 8/0012 |

OTHER PUBLICATIONS

Machine translation of KR-20130092855-A, Mar. 2025 (Year: 2025).*
Machine translation of DE-4012731-A, Mar. 2025 (Year: 2025).*
Machine translation of JP-04054966-A, Apr. 2025 (Year: 2025).*

* cited by examiner

*Primary Examiner* — Geoffrey S Evans
(74) *Attorney, Agent, or Firm* — McHale & Slavin, P.A.

(57) ABSTRACT

A method for texturing of selected surfaces on a spinal implant. The implant is pretreated with an EDM process by passing the implant by an electrode along an axis, at a predetermined speed, voltage and current. The implant is further conditioned by $Al_2O_3$ grit blasting followed by an acidic solution bath and process water rinse, which yields a surface porosity and topography conducive to osseointegration on the surface of the spinal implant.

8 Claims, 11 Drawing Sheets

METHOD OF TREATING A MEDICAL IMPLANT SURFACE FOR OSSEOINTEGRATION

PRIORITY CLAIM

In accordance with 37 C.F.R. § 1.76, a claim of priority is included in an Application Data Sheet filed concurrently herewith. Accordingly, the present application claims the priority date of U.S. Provisional Patent Application No. 63/169,652 filed Apr. 1, 2021, entitled "METHOD OF CREATING A SURFACE FOR OSSEOINTEGRATION", the contents of which are incorporated herein by reference.

FIELD OF THE INVENTION

The field of the invention is medical implants and, more specifically, to a method for treating a medical implant surface for osseointegration by pretreating with an electrical discharge machine and finishing with an $Al_2O_3$ grit finishing process to yield a surface porosity and topography conducive to osseointegration on the surface of the spinal implant.

BACKGROUND OF THE INVENTION

Artificial implants are fixated by the human body through functional ankylosis. Once an artificial implant is installed, a functional connection between living bone and the implant is required for positioning longevity. Spinal fusion is commonly used when an individual is suffering from a degenerative disc or severe spinal injury. Fusion is used to stabilize the spine and protect the nerves. Stabilization may be from the use of plates, rods, screws, cages and the like implants. Bone or bone like material placed between bone and the implant furthers the stabilization as bone material attaches to the implant.

Maintaining the implant in position becomes critical, and any improvement in the bone material or implant to enhance attachment is highly beneficial. The spinal implants provide an initial step in stabilizing and longtime positioning, wherein the implant becomes fused to the bone. In such instances, the implant may include a design that facilitates growth, or may be used to hold a bone growth material to further expedite the fusion. Bone growth material may be taken from the individual's own body (autograft), from a cadaver (allograft), from an animal (xenograft), or employ a material that promotes spinal fusion, such as bone morphogenetic proteins and demineralized bone matrix.

Osteointegration is the structural and functional connection between growing bone and the surface of a spinal artificial implant, and commonly relies upon autograft. Osteoinduction refers to pluripotent cells that are stimulated to develop into the bone-forming cell lineage to cause new bone to form where bone does not already exist, and commonly relies upon autograft and bone morphogenetic proteins. Osteoconduction refers to the way bone graft material builds a scaffold, the framework for bone to fill inside. An osteoconductive material permits bone growth on its surface or down into pores, channels or pipes.

Polyetheretherketone (PEEK) is a known material for use in constructing implants, such as a cage for use with bone graft. PEEK's biocompatibility, particularly when used as a vertebral cage, is well known in the industry, but lacks sufficient strength for the current trend of spinal implants which are adjustable for height and lordotic angles and can be bioinert.

SUMMARY OF THE INVENTION

Disclosed is a method for texturing selected surfaces for osseointegration of spinal implants. The method includes an implant treatment step using an EDM process wherein an implant passes along an axis of an electrode at a predetermined speed, voltage and current to texture the surface. The implant is further conditioned by $Al_2O_3$ grit blasting, followed by a acidic solution bath and process water rinse to yield a surface porosity and topography conducive to osseointegration.

The method includes the use of a fluid tank containing a volume of dielectric fluid having a movable support constructed and arranged to move a spinal implant through the dielectric fluid along an axis at a predetermined speed. In a preferred embodiment, a brass electrode is placed in close proximity to a selected surface of the spinal implant provides the surface texturing. A controller having an adjustable voltage and current causes the electrode to yield a surface porosity and topography of about 5 microns consisting of nano, micro, and macro structures. The implant is further conditioned by a nitric acid bath to yield a surface porosity and topography free from electro slag wherein nano, micro, and macro structures of about 5 microns in size makes the implant conducive to osseointegration.

The objective of the invention is to teach a method of treating a medical implant to yield a surface porosity and topography conducive to osseointegration.

Another objective of the invention is to teach a method of treating spinal implants with an EDM process and finishing process capable of yielding an average surface roughness of 5 microns minimum under 10× optic and less than 5 microns under 20× optic.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DESCRIPTION OF THE INVENTION

Figure 1:
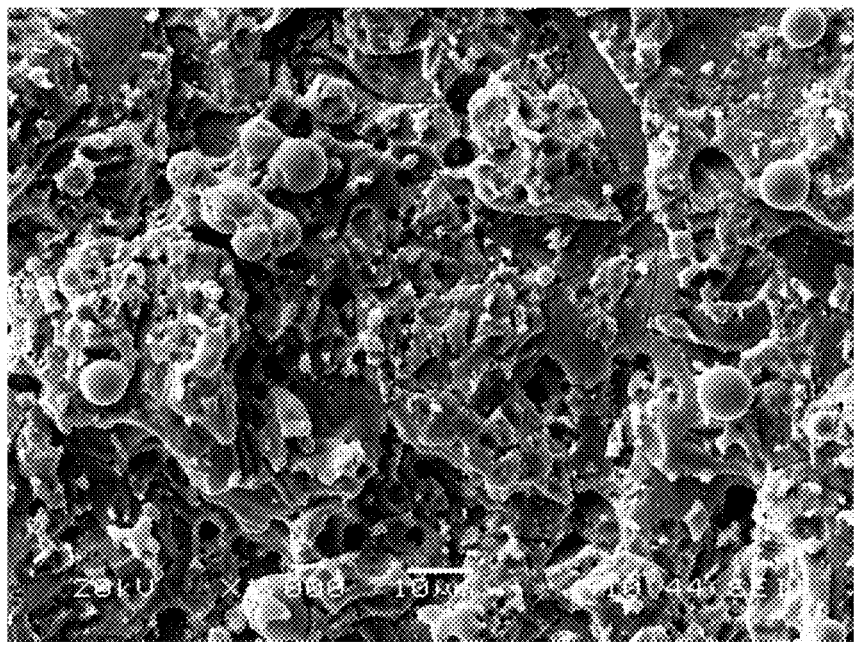
FIG. 1 is a photo of a treated surface magnified 1000×.

An embodiment of the instant invention is disclosed herein; however, it is to be understood that the disclosed embodiment is merely exemplary of the invention, which may be embodied in various forms. Therefore, specific functional and structural details and steps disclosed herein are not to be interpreted as limiting, but merely as a basis for the claims and as a representation basis for teaching one skilled in the art to variously employ the present invention in virtually any appropriately detailed structure.

Disclosed is a method of creating a surface topography conducive to osseointegration in conductive metallic devices for use in surgical procedures. EDM (electro discharge machining) is an errosive production method used in the process of generating a specific shape in conductive metallic materials. When operated at specific parameters (charge and speed), the EDM process yields a surface porosity and topography conducive to osseointegration (the formation and adhesion of bony cellular activity).

Although EDM has widely been used as a method of machining, it is believed that the process for the specific purpose of creating an osseoinductive surface is novel as it applies to medical implants, as only certain aspects of the implant need to be textured, and the surface to be textured must be sized accordingly. Attached are high magnification images of a surface resulting from use of the described method. As shown, the method produces a surface with the essential nano, micro, and macro structures necessary to promote healthy osseointegration.

In operation, an electrode is spaced apart from an implant positioned in a dielectric fluid. In one embodiment the fluid has a resistivity of 1 megOhms (1,000,000 ohms) or greater. Voltage is applied to the electrode and implant; as voltage is increased, the intensity of the electric field between the electrode and implant becomes greater, which causes a dielectric break down and produces an electric arc. In a preferred embodiment the electrode is brass and can have a positive polarity or a negative polarity. When the polarity is negative, the spark passes from an electrode to the implant to be textured. When the polarity is positive, the spark passes from the implant to be textured to the electrode. The controller oversees voltage and electrical current to the electrode and implant, which melts the extreme outer layer of the implant, forming microscopic craters proportional in size and spacing to the energy supplied and the frequency of generation. The result is an extremely precise, predictable and controllable texture on the implant to be treated. As a result, material is removed from the implant. Once the voltage is stopped, the removed material is carried away. Adding new dielectric liquid provides a flushing. While brass the preferred electrode other materials, including tungsten, can be used.

The voltage and frequency is continuous, stepwise, back and forth and/or intermittently at the same or various intervals, frequencies and/or distances. The method is calculated to provide a surface porosity that includes essential nano, micro, and macro structures to promote osseointegration.

The EDM treated implant results in nano, micro, and macro structures with an Ra of about 5 microns including electrode slag. A finishing step is to grit blast with Alodur White $Al_2O_3$, or equivalent, and post process through and acidic solution bath, preferably a solution 25% Nitric Acid and 75% water, followed by rinsing with process water. Blasting should occur with a nozzle distance of 8"+/−1" from the implant being treated with a pressure of 25 psi+ 2/−0 for a period of 5 seconds+2/−0. The average surface roughness of each implant (average of ≥2 locations), as indicated by Ra value, shall be 5.0 microns minimum under 10× optic and less than 5.0 microns under 20× optic. The Ra value shall be determined by imaging the surface with the Keyence Laser Scanning Microscope with both 10× optic/1× digital zoom and 20× optic/2× digital zoom.

The output shall be analyzed utilizing the Surface Roughness technique with the following settings:

Filter: λc=8.0 mm (10× optic/1× digital zoom)

Region=Area 8000 um×1000 um (10× optic/1× digital zoom) or maximum available surface area if part geometry/size does not permit scanning a region of 8000 um×1000 um Filter λc=0.08 mm (20× optic/2× digital zoom)

Region=Area 200 um×200 um (20× optic/2× digital zoom)

The $Al_2O_3$ macro-blasted surface shall visually (e.g. 10×) have a matte appearance, a homogenous grey coloration, and the finish be visually absent of residual media.

The method for electrical discharge texturing of selected surfaces on a spinal implant comprises: a fluid tank containing a volume of dielectric fluid; a support holding a spinal implant mounted within the fluid tank; a controller for moving the support along an axis at a predetermined speed; a brass electrode affixed within the fluid tank and spaced apart from the support, the electrode having a proximal end disposed below the surface level of the dielectric fluid and a distal end in close proximity to a first selected surface of the spinal implant; applying a predetermined voltage causing a spark between the electrode and implant; and moving the implant for interaction with the electrode to cause a spark for a predetermined period of time. The implant is grit blasted with $Al_2O_3$, processed through a solution containing 25% Nitric Acid and water, and then rinsed with process water such as deionized water, wherein the method yields a surface porosity and topography conducive to osseointegration on the surface of the implant.

Figure 2:
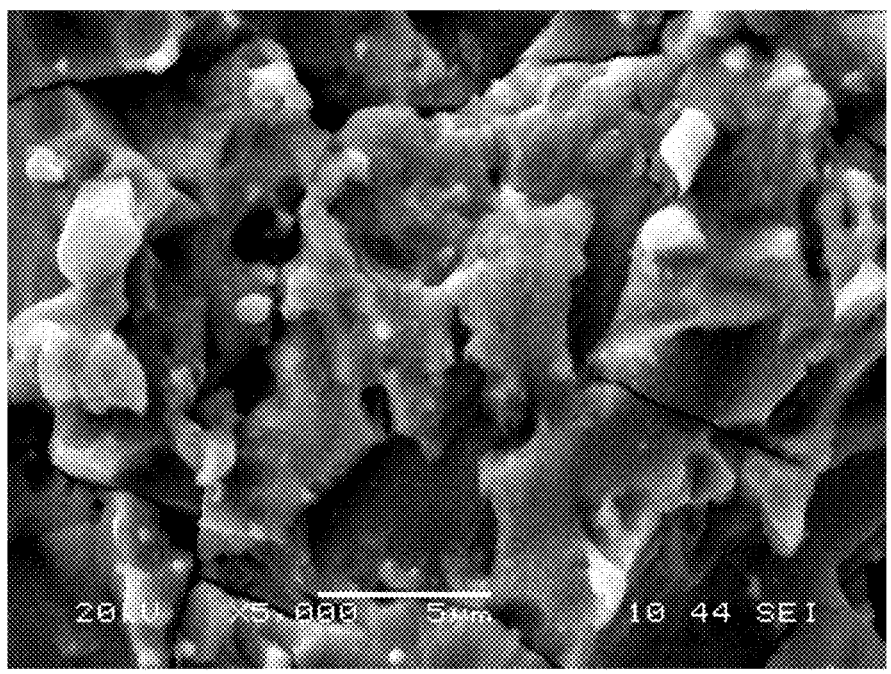
FIG. 2 is a photo of a treated surface magnified 5000×.

Referring to FIGS. 1 and 2, set forth is a general photo of an EDM treated surface magnified 1000×, FIG. 2 depicts the EDM treated surface magnified 5000×.

Figure 3A:
FIG. 3A is a photo of a spinal implant device pretreated with EDM.
Figure 3B:
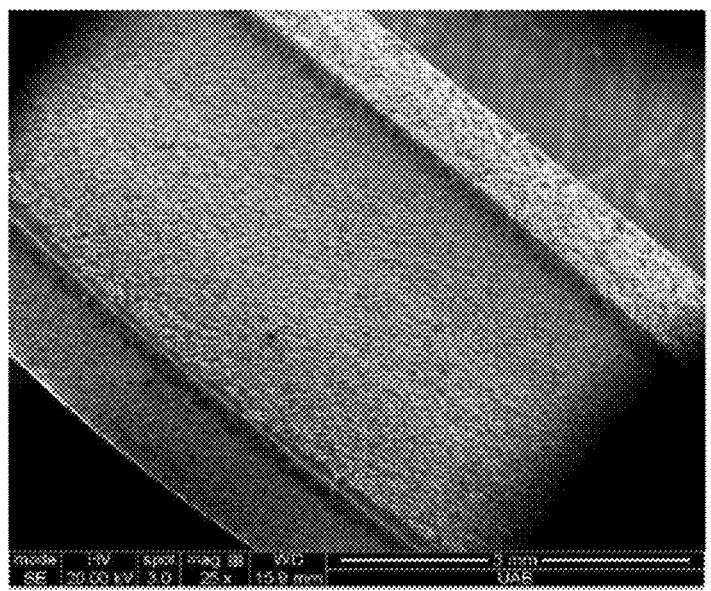
FIG. 3B is a photo of the spinal implant device shown in FIG. 3A magnified 25×.
Figure 3C:
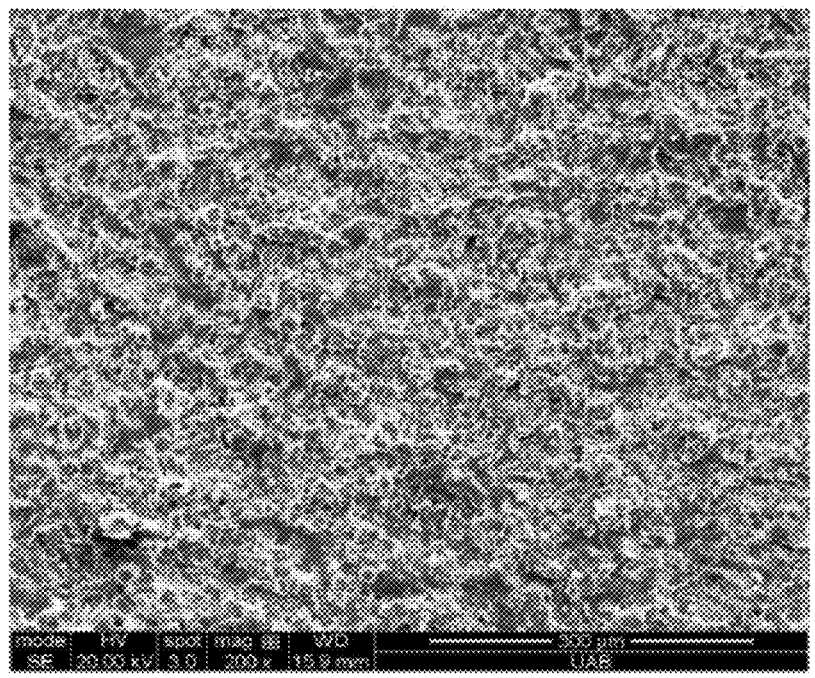
FIG. 3C is a photo of the spinal implant device shown in FIG. 3A magnified 200×.
Figure 3D:
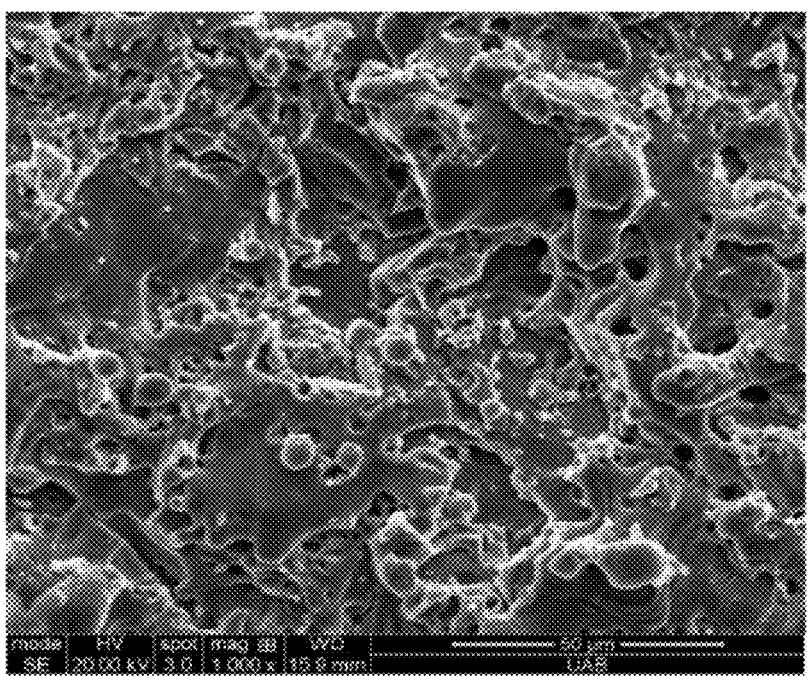
FIG. 3D is a photo of the spinal implant device shown in FIG. 3A magnified 1000×.
Figure 3E:
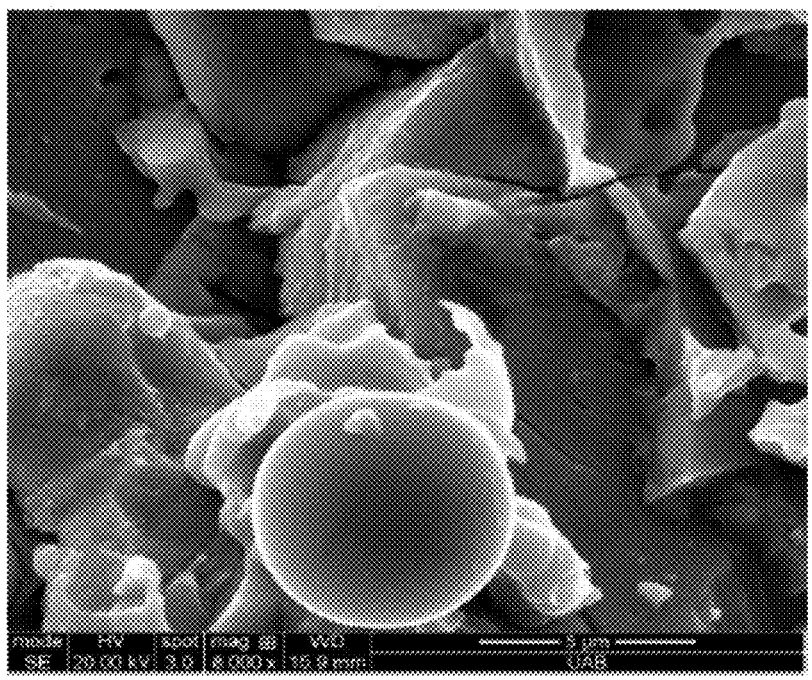
FIG. 3E is a photo of the spinal implant device shown in FIG. 3A magnified 8000×.
Figure 3F:
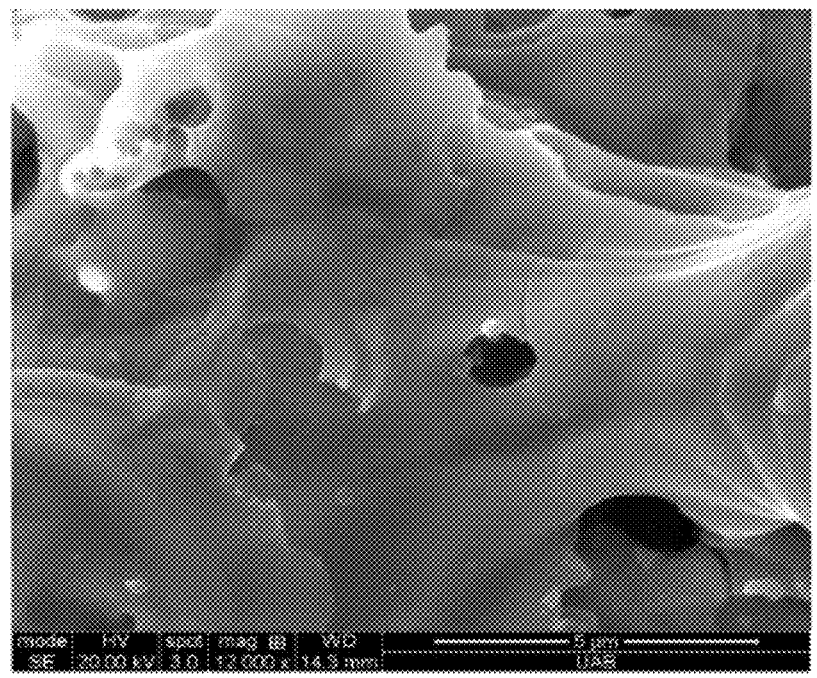
FIG. 3F is a photo of the spinal implant device shown in FIG. 3A magnified 12000×.
Figure 3G:
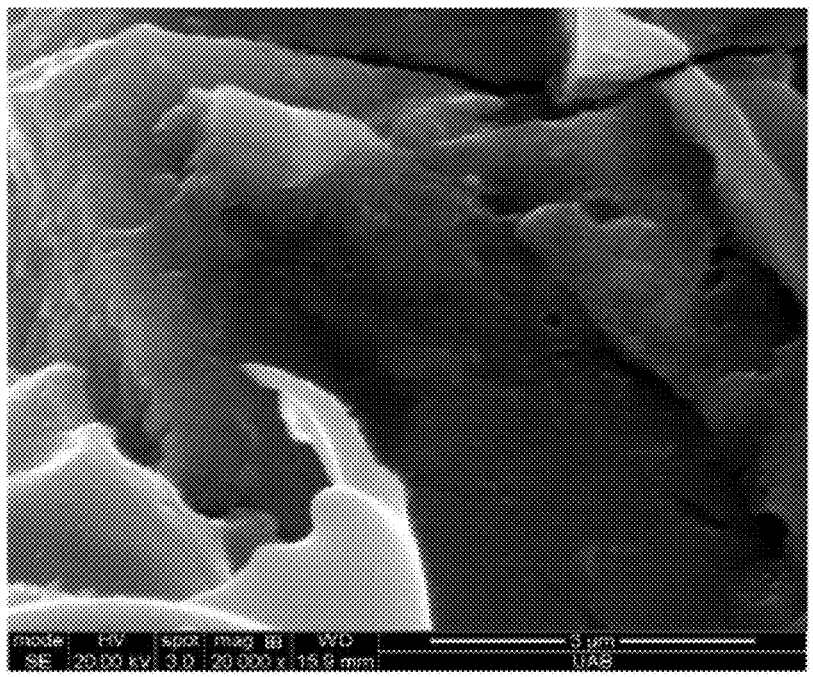
FIG. 3G is a photo of the spinal implant device shown in FIG. 3A magnified 20000×.
Figure 3H:
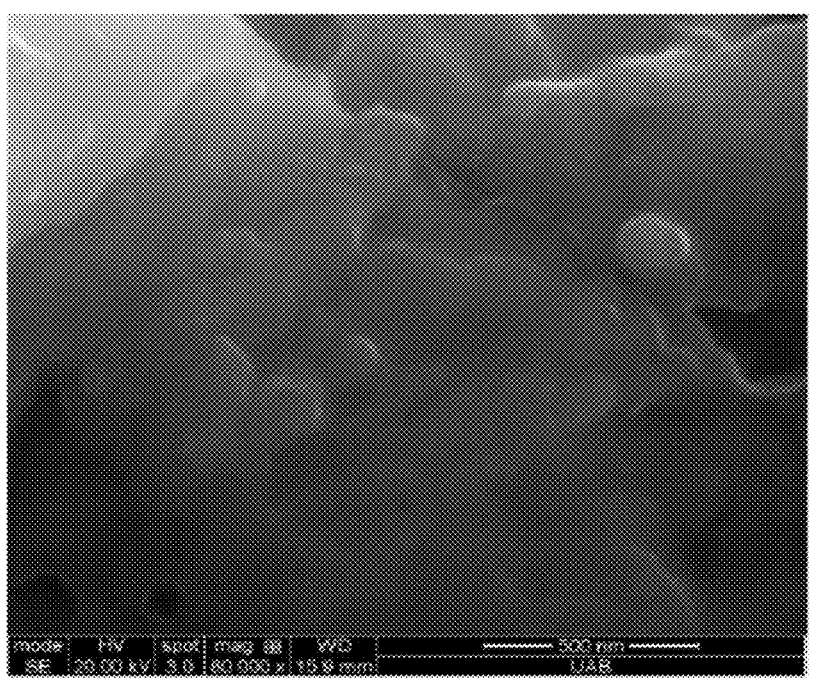
FIG. 3H is a photo of the spinal implant device shown in FIG. 3A magnified 80000× along a first location.
Figure 3I:
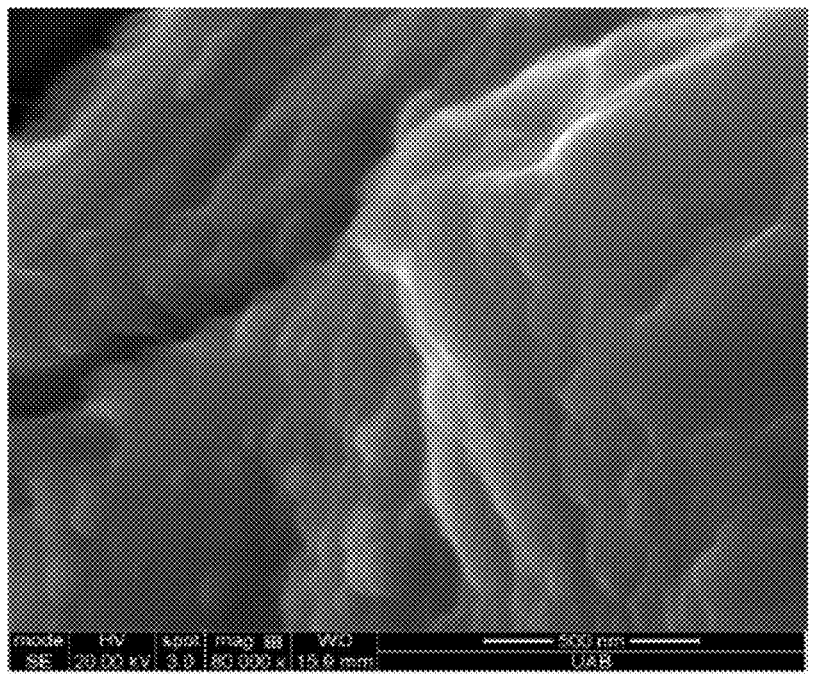
FIG. 3I is a photo of the spinal implant device shown in FIG. 3A magnified 80000× along a second location.
Figure 3J:
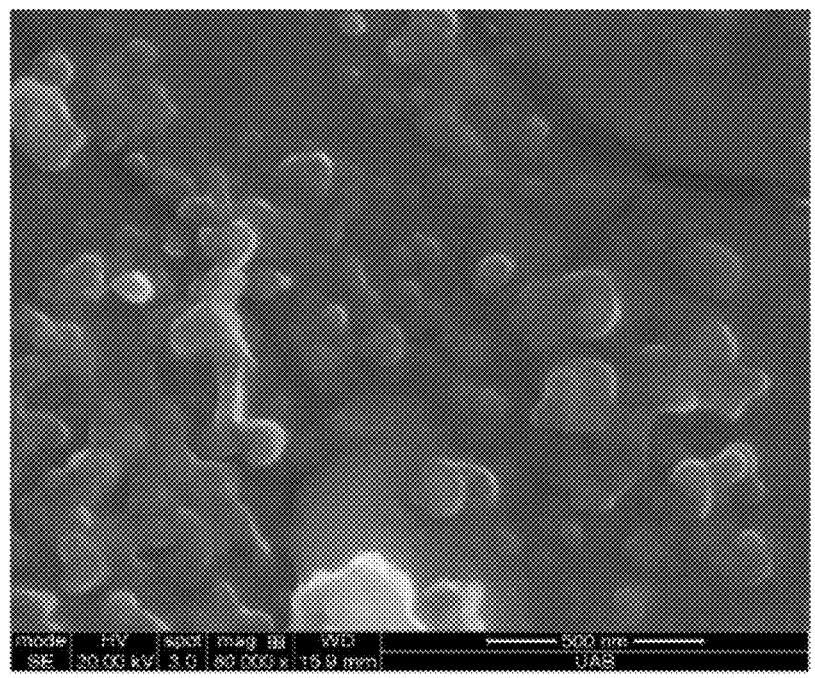
FIG. 3J is a photo of the spinal implant device shown in FIG. 3A magnified 80000× along a third location.

Referring to FIGS. 3A-3J, the series of photographs depicts sample 1. The medical implant is constructed from tungsten and treated with the EDM process as set forth in this specification, rendering the texture shown in the photographs. FIG. 3B is a photo of the implant in FIG. 3A magnified 25× with a scale of 3 mm. FIG. 3C is a photo of the implant in FIG. 3A magnified 200× with a scale of 300 microns. FIG. 3D is a photo of the implant in FIG. 3A magnified 1000× with a scale of 50 microns. FIG. 3E is a photo of the implant in FIG. 3A magnified 8000× with a scale of 5 microns, the ball is a brass slag from the EDM process to be removed by the finishing process of grit blasting and acidic solution bath, preferably a solution consisting of 25% nitric acid and 75% distilled or deionized water. FIG. 3F is a photo of the implant in FIG. 3A magnified 12000× with a scale of 5 microns. FIG. 3G is a photo of the implant in FIG. 3A magnified 20000× with a scale of 3 microns. FIG. 3H is a photo of FIG. 3A magnified 80000× along a first location with a scale of 500 nm; FIG. 3I is a photo of the implant in FIG. 3A magnified 80000× along a second location with a scale of 500 nm; FIG. 3J is a photo of the implant shown in FIG. 3A magnified 80000× along a third location with a scale of 500 nm.

Figure 4A:
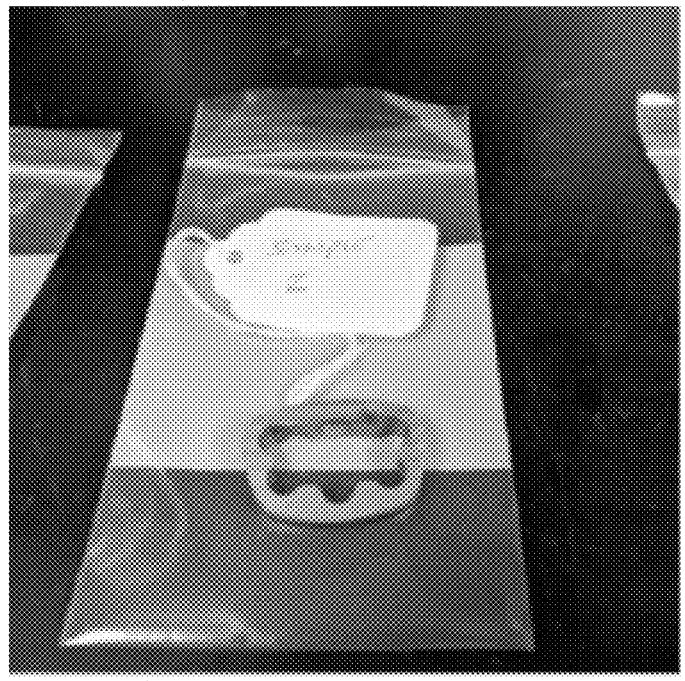
FIG. 4A is a photo of a spinal implant device treated with aluminum oxide grit.
Figure 4B:
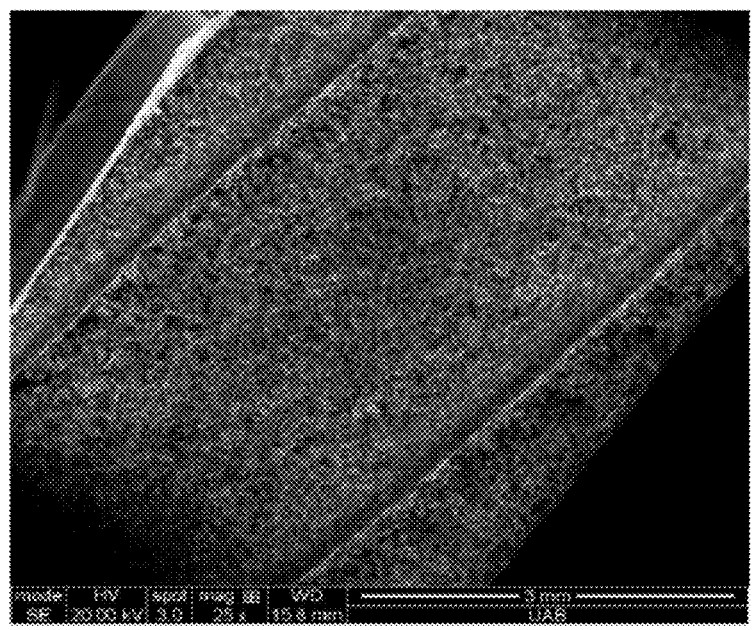
FIG. 4B is a photo of the spinal implant device shown in FIG. 4A magnified 25×.
Figure 4C:
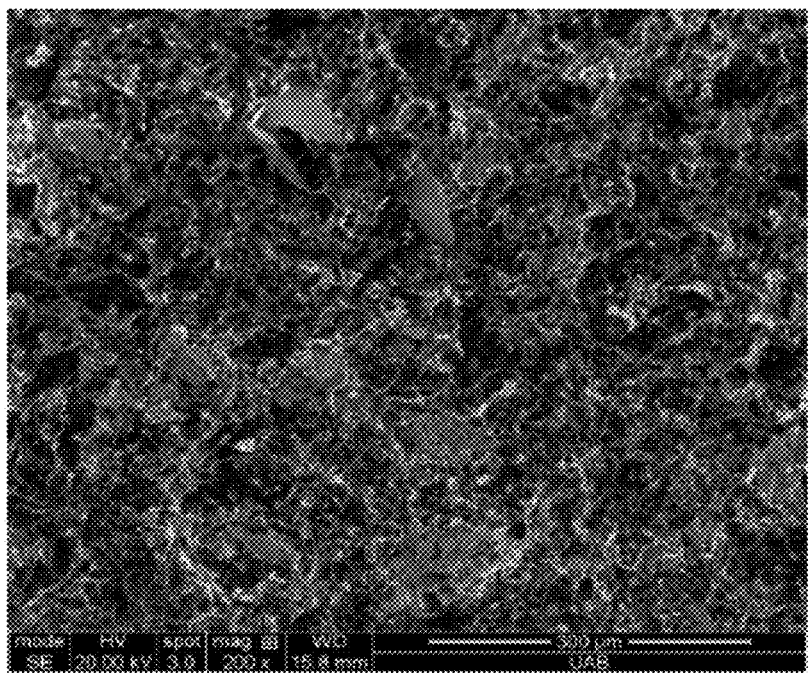
FIG. 4C is a photo of the spinal implant device shown in FIG. 4A magnified 200×.
Figure 4D:
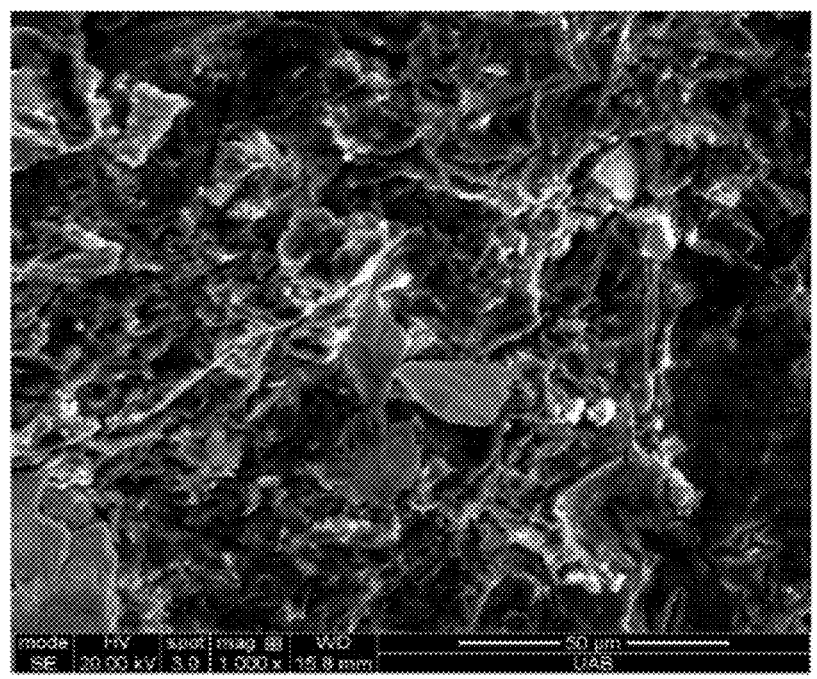
FIG. 4D is a photo of the spinal implant device shown in FIG. 4A magnified 1000×.
Figure 4E:
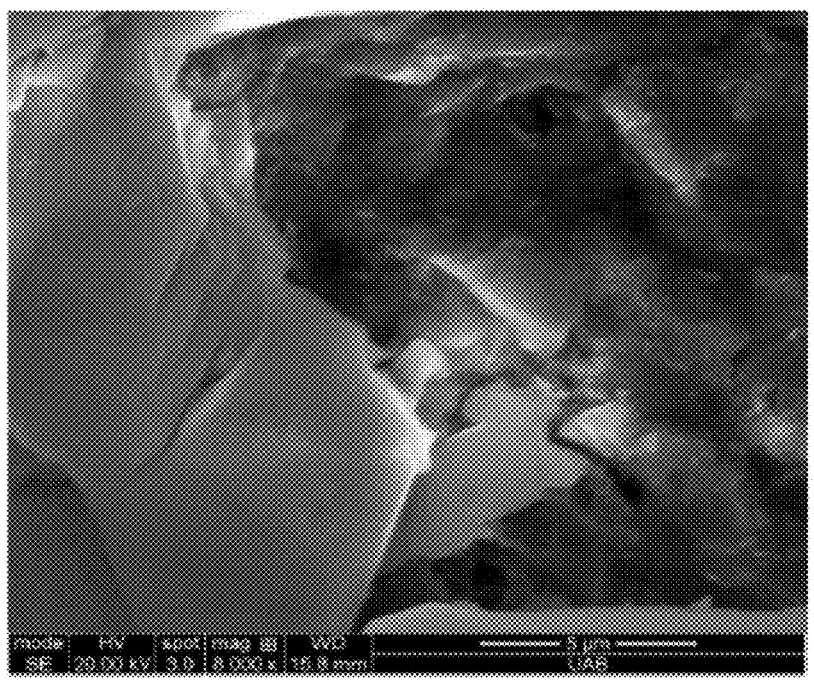
FIG. 4E is a photo of the spinal implant device shown in FIG. 4A magnified 8000×.
Figure 4F:
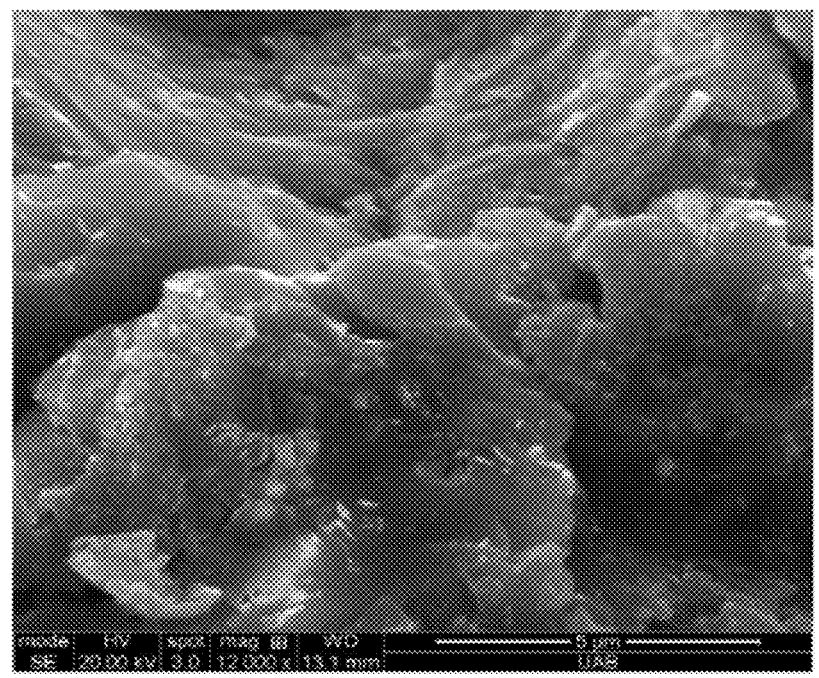
FIG. 4F is a photo of the spinal implant device shown in FIG. 4A magnified 12000×.
Figure 4G:
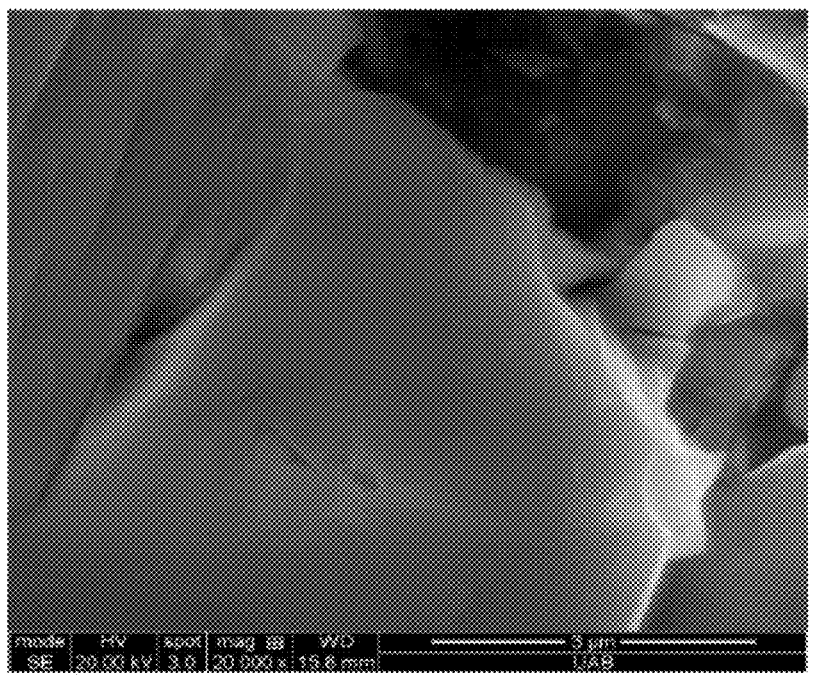
FIG. 4G is a photo of the spinal implant device shown in FIG. 4A magnified 20000×, WD 13.1 mm.
Figure 4H:
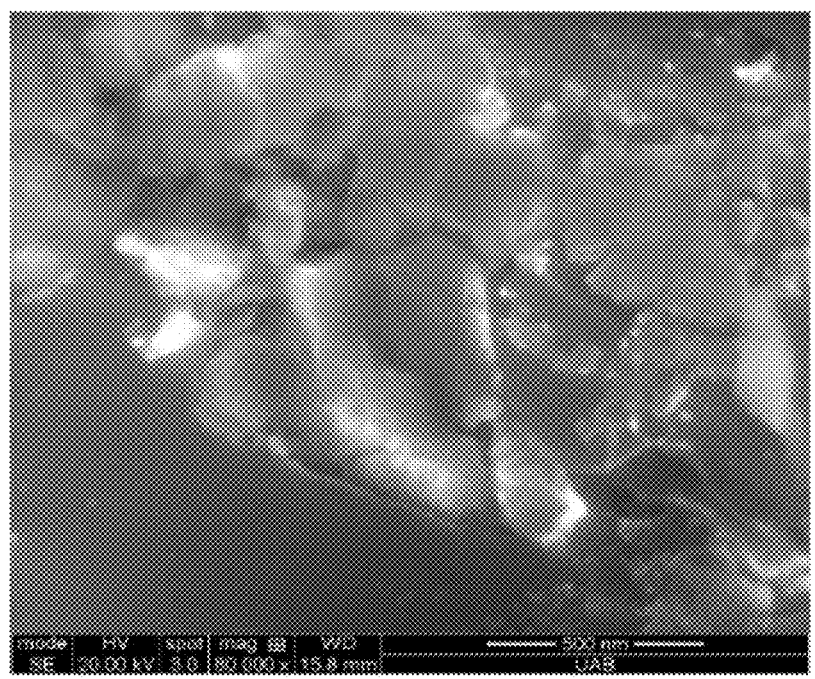
FIG. 4H is a photo of the spinal implant device shown in FIG. 4A magnified 80000×, WD 15.8 mm.
Figure 4I:
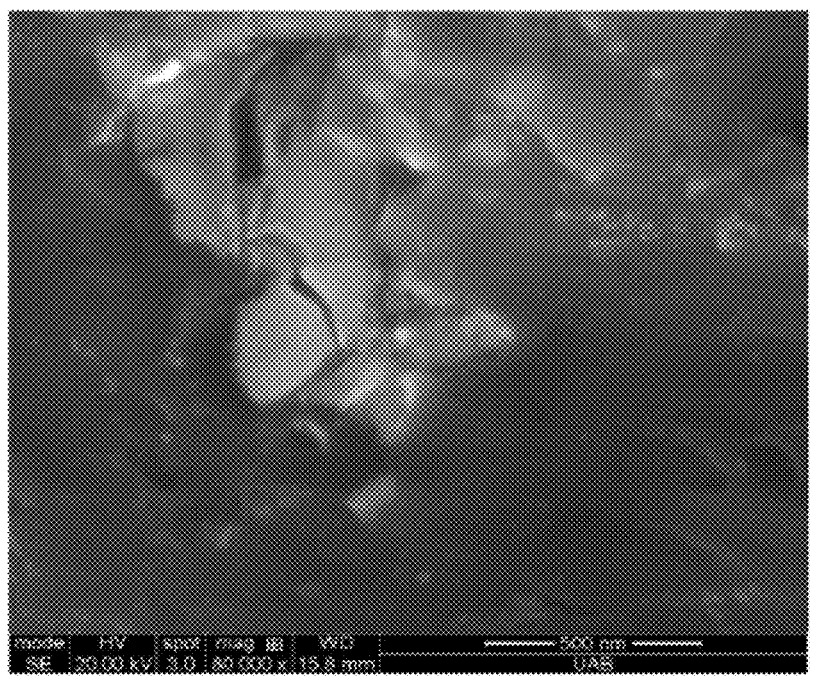
FIG. 4I is a photo of the spinal implant device shown in FIG. 4A magnified 80000× along a first location.

FIG. 4A is a photo of the spinal implant first depicted in FIGS. 3A-3J, wherein the EDM process had been applied and then finished with an $Al_2O_3$ finishing process consisting of grit blasting with nitric acid bath, followed with a rinse using process water preferably said process water is deionized or distilled having a conductivity greater than 1 megOhm. FIG. 4B is a photo of the spinal implant shown in FIG. 4A magnified 25× with a scale of 3 mm. FIG. 4C is a photo of the spinal implant device shown in FIG. 4A magnified 200× with a scale of 300 microns. FIG. 4D is a photo of the spinal implant device shown in FIG. 4A magnified 1000× with a scale of 50 microns. FIG. 4E is a photo of the spinal implant device shown in FIG. 4A magnified 8000× with a scale of 5 microns. FIG. 4F is a photo of the spinal implant device shown in FIG. 4A magnified 12000× with a scale of 5 microns. FIG. 4G is a photo of the spinal implant device shown in FIG. 4A magnified 20000×, WD 13.1 mm, with a scale of 5 microns. FIG. 4G is a photo of the spinal implant device shown in FIG. 4A magnified 20000×, WD 15.8 mm, with a scale of 3 microns. FIG. 4H is a photo of the spinal implant device shown in FIG. 4A magnified 80000× along a first location with a scale of 500 nm. And FIG. 4I is a photo of the spinal implant device shown in FIG. 4A magnified 80000× along a second location with a scale of 5 nm.

The use of the word "a" or "an" when used in conjunction with the term "comprising" in the claims and/or the specification may mean "one," but it is also consistent with the meaning of "one or more" or "at least one." The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

It is to be understood that while a certain form of the invention is illustrated, it is not to be limited to the specific steps herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Various modifications of the described modes for carrying out the invention which are obvious to those skilled in the art are intended to be within the scope of the following claims.

What is claimed is:

1. A method of treating surfaces on medical implants for osseointegration comprising the steps of:
   placing an implant in a body of dielectric water;
   juxtapositioning an electrode to the implant;
   exposing the implant surface to said electrode through an EDM process with a voltage for a period of time to obtain a porosity on the surface of the implant;
   grit blasting a surface of the implant to obtain an average surface roughness Ra value of 5 microns;
   bathing the implant with an acidic solution;
   rinsing the implant with process water to yield a surface porosity and topography conducive to osseointegration on the surface of the spinal implant.

2. The method of treating the surface of medical implants according to claim 1 including the step of verifying said surface roughness Ra value of 5 microns minimum is under 10× optic and less than 5.0 microns under 20× optic.

3. The method of treating the surface of medical implants according to claim 2 wherein said step of verifying surface roughness shall be determined by imaging the surface with a Laser Scanning Microscope with both a 10× optic/1× digital zoom and a 20× optic/2× digital zoom.

4. The method of treating the surface of medical implants according to claim 1 wherein said porosity and topography includes nano, micro, and macro structures conducive to osseointegration.

5. The method of treating the surface of medical implants according to claim 1 wherein said grit blasting with $Al_2O_3$ is with a nozzle distance of 8 inches+/−1 inch from the implant being treated with a pressure of 25 psi+2/−0 for a period of 5 sec+2/−0.

6. The method of treating the surface of medical implants according to claim 1 wherein said acidic solution is 25% nitric acid and 75% deionized or distilled water.

7. The method of treating the surface of medical implants according to claim 1 wherein said electrode is brass.

8. The method of treating the surface of medical implants according to claim 1 wherein said process water has a resistivity greater than 1 megOhm.

* * * * *